(12) United States Patent
Shiba et al.

(10) Patent No.: US 11,051,690 B2
(45) Date of Patent: Jul. 6, 2021

(54) OPHTHALMOLOGICAL IMAGE PROCESSING APPARATUS AND STORAGE MEDIUM

(71) Applicant: NIDEK CO., LTD., Aichi (JP)

(72) Inventors: Ryosuke Shiba, Aichi (JP); Tetsuya Kano, Aichi (JP); Naoki Takeno, Aichi (JP)

(73) Assignee: NIDEK CO., LTD., Aichi (JP)

( * ) Notice: Subject to any disclaimer, the term of this patent is extended or adjusted under 35 U.S.C. 154(b) by 352 days.

(21) Appl. No.: 16/282,435

(22) Filed: Feb. 22, 2019

(65) Prior Publication Data

US 2019/0269319 A1 Sep. 5, 2019

(30) Foreign Application Priority Data

Mar. 5, 2018 (JP) .............................. JP2018-039165

(51) Int. Cl.
| | |
|---|---|
| *A61B 3/14* | (2006.01) |
| *A61B 3/10* | (2006.01) |
| *A61B 3/12* | (2006.01) |
| *A61B 3/00* | (2006.01) |
| *G06T 5/50* | (2006.01) |
| *G01B 9/02* | (2006.01) |

(52) U.S. Cl.
CPC ................ *A61B 3/102* (2013.01); *A61B 3/12* (2013.01); *A61B 3/14* (2013.01); *A61B 3/0058* (2013.01); *G01B 9/02091* (2013.01); *G06T 5/50* (2013.01); *G06T 2207/30041* (2013.01)

(58) Field of Classification Search
CPC .. A61B 3/14; A61B 3/12; A61B 3/102; A61B 3/10; A61B 3/00; G06T 7/33; G06T 5/50
USPC ................................ 351/206, 246, 205, 200
See application file for complete search history.

(56) References Cited

U.S. PATENT DOCUMENTS 10,152,807 B2 * 12/2018 Kuno ....................... G06T 7/50
2011/0205490 A1 8/2011 Murata et al.

FOREIGN PATENT DOCUMENTS

JP 2011-172822 A 9/2011

* cited by examiner

*Primary Examiner* — Hung X Dang
(74) *Attorney, Agent, or Firm* — Sughrue Mion, PLLC (57) ABSTRACT

An ophthalmological image processing apparatus includes an image obtaining portion for obtaining ophthalmological image data, which is captured by an imaging unit, of a subject eye, and an image processing portion for processing the ophthalmological image data. The image processing portion uses a first front image of the subject eye in a first depth region to correct a second front image of the subject eye captured in a second depth region which is different from the first depth region. The first front image and the second front image are constructed based on the ophthalmological image data. The ophthalmological image processing apparatus can reduce an artifact which is generated in an ophthalmological image.

7 Claims, 8 Drawing Sheets

OPHTHALMOLOGICAL IMAGE PROCESSING APPARATUS AND STORAGE MEDIUM

CROSS-REFERENCE TO RELATED APPLICATION

This application claims priority from Japanese Patent Application No. 2018-039165 filed on Mar. 5, 2018, the entire subject-matter of which is incorporated herein by reference.

TECHNICAL FIELD

The present disclosure relates to an ophthalmological image processing apparatus and a storage medium storing an ophthalmological image processing program for processing an ophthalmological image captured by imaging a subject eye.

BACKGROUND

An optical coherence tomography (OCT), a fundus camera, a scanning laser ophthalmoscope (SLO), or the like is known as an ophthalmological imaging apparatus which captures an image of a subject eye (refer to JP-A-2011-172822).

In an ophthalmological image captured by imaging the subject eye with the ophthalmological imaging apparatus, an artifact is generated at a position of a retinal deep layer due to an influence of fluctuation or a shadow of a blood vessel portion of a retinal shallow layer.

SUMMARY

An object of the present disclosure is to provide an ophthalmological image processing apparatus and a storage medium storing an ophthalmological image processing program that can reduce an artifact which is generated in an ophthalmological image.

In order to solve the problems described above, the present disclosure includes the following configurations.

(1) An ophthalmological image processing apparatus that processes an ophthalmological image, includes:

an image obtaining portion configured to obtain ophthalmological image data, which is captured by an imaging unit, of a subject eye; and an image processing portion configured to process the ophthalmological image data, in which the image processing portion uses a first front image of the subject eye captured in a first depth region to correct a second front image of the subject eye captured in a second depth region which is different from the first depth region, and the first front image and the second front image are constructed based on the ophthalmological image data.

(2) A non-transitory computer readable recording medium storing an ophthalmological image processing program used in an ophthalmological image processing apparatus that processes an ophthalmological image, in which the ophthalmological image processing program is executed by a controller of the ophthalmological image processing apparatus to cause the ophthalmological image processing apparatus to perform:

obtaining ophthalmological image data, which is captured by an imaging unit, of a subject eye; and using a first front image of the subject eye captured in a first depth region to correct a second front image of the subject eye captured in a second depth region which is different from the first depth region, and the first front image and the second front image are constructed based on the ophthalmological image data.

DETAILED DESCRIPTION

Embodiment

An embodiment according to the present disclosure will be described. An ophthalmological image processing apparatus (for example, an ophthalmological image processing apparatus 1) of a present embodiment processes an ophthalmological image captured by imaging a subject eye. The ophthalmological image processing apparatus includes an image obtaining portion (for example, an image obtaining portion 71), and an image processing portion (for example, an image processing portion 72). The image obtaining portion obtains ophthalmological image data of the subject eye which is imaged by an imaging unit (for example, an imaging apparatus 10). The image processing portion processes the ophthalmological image data. For example, the image processing portion uses a first front image of the subject eye captured in a first depth region to correct a second front image captured in a second depth region which is different from the first depth region. For example, the image processing portion is capable of reducing Projection Artifact which is generated in a front image of a deep layer, by correcting the front image of the deep layer based on a front image of a shallow layer. For example, the front image is an En face image constructed based on the ophthalmological image data. For example, the En face is a surface which is horizontal with respect to a fundus surface, or a fundus two-dimensional horizontal tomographic surface.

The image processing portion may use the first front image to correct the second front image per a local area. For example, the image processing portion may correct the second front image per the local area which is set based on the first front image. For example, the image processing portion may detect a blood vessel position of the shallow layer from the front image of the shallow layer, and may correct the front image of the deep layer in accordance with a vicinity of the detected blood vessel position. Thereby, it is possible to efficiently reduce an artifact which is generated in the front image of the deep layer.

For example, the local area may be a section obtained by dividing an image into several blocks, or may be a section obtained by dividing the image into a shape of concentric circles. The local area may be a section obtained by dividing the image into any shape. For example, the image processing portion may divide the first front image and the second front image into a plurality of areas, and may correct the second front image of the corresponding area, using the first front image per the area. Thereby, it is possible to prevent the artifact from locally remaining, or the artifact from being erased too much.

The image processing portion may change a division position of the area, based on the first front image. For example, the division position of the image may be set in accordance with the blood vessel position which is detected from the first front image. Thereby, it is possible to efficiently reduce the local artifact. Moreover, the image processing portion may change the division position of the area, based on an imaging position of the ophthalmological image data. For example, the division position may be changed in accordance with the imaging position with a macula lutea as a center, or the imaging position with an optic papilla as a center.

The image processing portion may calculate a similarity degree between the first front image and the second front image of each local area. Therefore, the image processing portion may calculate a weight for each local area based on the similarity degree of the corresponding local area. For example, the weight is used in arithmetic operation processing for reducing the similarity degree between the first front image and the second front image.

For example, the similarity degree is calculated by a correlation or a difference between the first front image and the second front image. For example, SSD (sum of squared difference), SAD (sum of absolute difference), NCC (normalized cross-correlation), ZNCC (zero-mean normalized cross-correlation), or the like may be calculated. Moreover, a magnitude of a peak value of a phase only correlation (POC) may be used as an index of the similarity degree. Naturally, a dissimilarity degree may be calculated in replacement of the similarity degree.

The first front image that is used in correction of the second front image may be constructed based on the ophthalmological image data in a data region (for example, on a vitreous body side) which is shallower than a data region in which the second front image is constructed. For example, the data region in which the first front image is constructed may be an upper data region of the ophthalmological image data from an upper end of the data region in which the second front image is constructed. Thereby, it is possible to restrain an influence of a segmentation result of a retinal layer, for example, in comparison with a case where the data region in which the first front image is constructed is set to a specific retinal layer. At the time of performing the correction of the second front image, it is possible to reduce the influence of noise which is generated outside of the specific retinal layer.

The image processing portion may exclude a fixed noise area from the data region in which the first front image is constructed. For example, the fixed noise is noise or the like which is caused by an optical system of the imaging unit. For example, in a case where an OCT is used as the imaging unit, an area of fixed pattern noise which is generated in the vicinity of zero delay may be excluded. In this case, since the position of the fixed pattern noise on an OCT image is changed by the position of an actual image, for example, an exclusion area may be switched by an imaging mode in a case where the position of the zero delay is matched up with an anterior side (vitreous body side) of the fundus, or an imaging mode in a case where the position of the zero delay is matched up with a posterior side (choroid coat side) of the fundus.

For example, the imaging unit (for example, an imaging apparatus 10) may be an OCT, a fundus camera, an SLO, or the like. For example, the imaging unit includes an optical system that is capable of obtaining image data of which depths are different from each other in an imaging optical axis direction.

A processor of the ophthalmological image processing apparatus may execute an ophthalmological image processing program which is stored in a storage portion. For example, the ophthalmological image processing program includes an image obtaining step, and an image processing step. For example, the image obtaining step is a step of obtaining the ophthalmological image data of the subject eye which is imaged by the imaging unit. The image processing step is a step of using the first front image of the subject eye captured in the first depth region to correct the second front image captured in the second depth region which is different from the first depth region.

Example

The ophthalmological image processing apparatus of a present example will be described with reference to the drawings. The ophthalmological image processing apparatus 1 illustrated in FIG. 1 processes the image data captured by the imaging apparatus 10. For example, the ophthalmological image processing apparatus 1 includes the image obtaining portion 71, the image processing portion 72, a storage portion 73, a display control portion 74, a display portion 75, an operation portion 76, and the like. The image obtaining portion 71 obtains the image of the subject eye. The image obtaining portion 71 is connected to the imaging apparatus 10 through a wired communication unit or a wireless communication unit. For example, the image obtaining portion 71 receives the ophthalmological image from the imaging apparatus 10 through the communication unit, and stores the ophthalmological image in the storage portion 73 or the like. The image obtaining portion 71 may obtain the ophthalmological image from an external storage apparatus such as an HDD or a USB memory which is connected through the communication unit.

Figure 1:
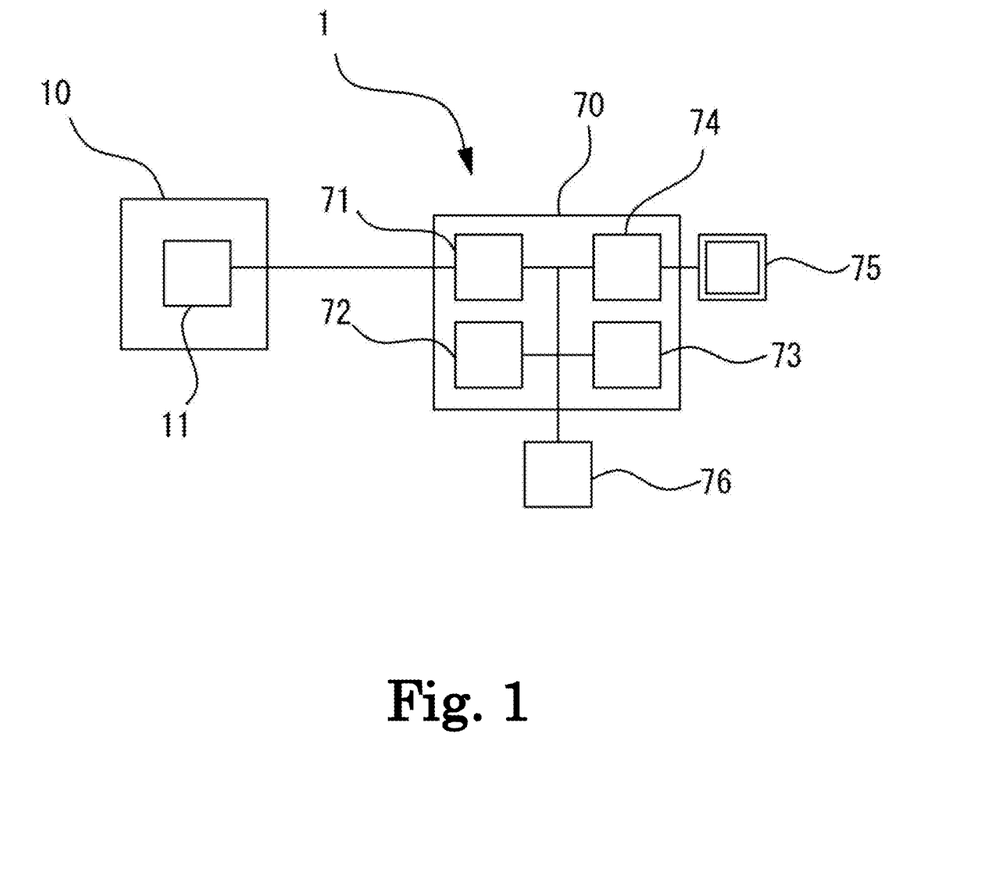
FIG. 1 is a block diagram illustrating an outline of an ophthalmological image processing apparatus.

For example, the image processing portion 72 performs image processing or the like with respect to the ophthalmological image. Details of the image processing will be described later. A processing result due to the image processing portion 72 is transmitted to the display portion 75, the storage portion 73, or the like.

The storage portion 73 stores various programs relating to a control of the ophthalmological image processing apparatus 1, various image data, the processing results, and the like. The display control portion 75 controls a display of the display portion 74. The display portion 75 displays the image obtained by the image obtaining portion 71, the processing result due to the image processing portion 72, and the like. The display portion 75 may be a touch panel type display. In this case, the display portion 75 also serves as an operation portion 76.

The image obtaining portion 71, the image processing portion 72, the storage portion 73, and the display control portion 74 may be realized, for example, by executing various programs with a controller (for example, a CPU or the like) 70 of a computer which is used as an ophthalmological image processing apparatus 1, or may be provided as control boards which are independent from each other.

The ophthalmological image processing apparatus 1 may be a personal computer. For example, a desktop PC, a notebook PC, or a tablet PC may be used as an ophthalmological image processing apparatus 1. Naturally, the ophthalmological image processing apparatus 1 may be a server. The ophthalmological image processing apparatus 1 may be a computer which is housed in an inner portion of the imaging apparatus or the like.

Imaging Unit

Figure 2:
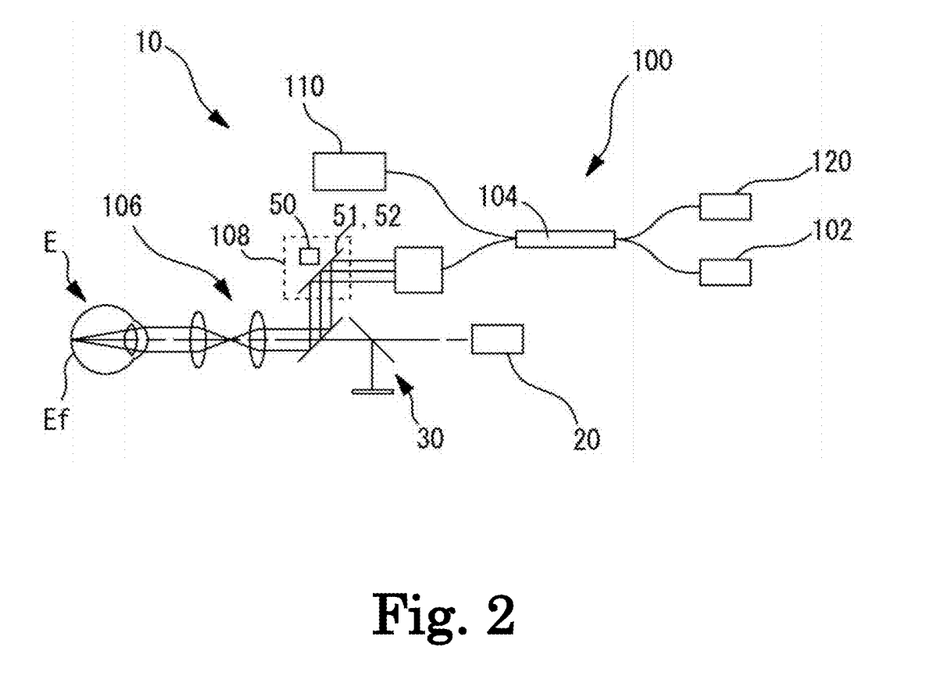
FIG. 2 is a diagram illustrating an example of an optical system of an OCT apparatus.

Hereinafter, an outline of an imaging unit 10 will be described based on FIG. 2. For example, the imaging unit 10 includes an OCT optical system 100. For example, the imaging unit 10 irradiates a subject eye E with measurement light, and obtains an OCT signal which is obtained by reflective light thereof and the measurement light.

OCT Optical System

The OCT optical system 100 irradiates the subject eye E with the measurement light, and detects an interference signal between the reflective light thereof and reference light. For example, the OCT optical system 100 mainly includes a measurement light source 102, a coupler (optical divider) 104, a measurement optical system 106, a reference optical system 110, a detector 120, and the like. A detailed configuration of the OCT optical system may refer to, for example, JP-A-2015-131107.

The OCT optical system 100 is an optical system of a so-called optical coherence tomography (OCT). The OCT optical system 100 divides light which is emitted from the measurement light source 102 into the measurement light (sample light) and the reference light by the coupler 104. The divided measurement light is guided to the measurement optical system 106, and the divided reference light is guided to the reference optical system 110, respectively. The measurement light is guided to a fundus Ef of the subject eye E through the measurement optical system 106. Thereafter, the detector 120 receives interference light due to composition of the measurement light which is reflected by the subject eye E, and the reference light.

For example, the measurement optical system 106 includes a scanning portion (for example, an optical scanner) 108. For example, the scanning portion 108 may be provided in order to cause the measurement light to be scanned in an XY direction (transverse direction) on the fundus. For example, the controller 70 controls an action of the scanning portion 108 based on scanning position information which is set, and obtains the OCT signal based on a light-receiving signal which is detected by the detector 120. The reference optical system 110 generates the reference light that is composed with the reflective light which is obtained by the reflection of the measurement light on the fundus Ef. The reference optical system 110 may be a Michelson type or a Mach-Zehnder type.

The detector 120 detects an interference state between the measurement light and the reference light. In the case of a Fourier-domain OCT, spectrum intensity of the interference light is detected by the detector 120, and a depth profile (A scan signal) in a predetermined range is obtained by Fourier transform with respect to spectrum intensity data.

As an imaging apparatus 10, for example, a Spectral-domain OCT (SD-OCT), a Swept-source OCT (SS-OCT), a Time-domain OCT (TD-OCT), or the like may be used.

Front Imaging Optical System

For example, a front imaging optical system 20 images the fundus Ef of the subject eye E from a front direction (for example, an optical axis direction of the measurement light), and obtains a front image of the fundus Ef. For example, the front imaging optical system 20 may have an apparatus configuration of a scanning laser ophthalmoscope (SLO) (for example, refer to JP-A-2015-66242), or may have a configuration of a so-called fundus camera type (refer to JP-A-2011-10944). The OCT optical system 100 may also serve as a front imaging optical system 200, and the front image may be obtained based on a detection signal from the detector 120.

Fixation Target Projection Portion

A fixation target projection portion 30 has an optical system for inducing a sight line direction of the eye E. The fixation target projection portion 30 has a fixation target which is presented to the eye E, and is capable of inducing the eye E. For example, the fixation target projection portion 30 has a visible light source that emits visible light, and two-dimensionally changes a presentation position of the fixation target. Thereby, the sight line direction is changed, and as a result, an obtainment region of the OCT signal is changed.

Obtainment of OCT Signal

Figure 3A:
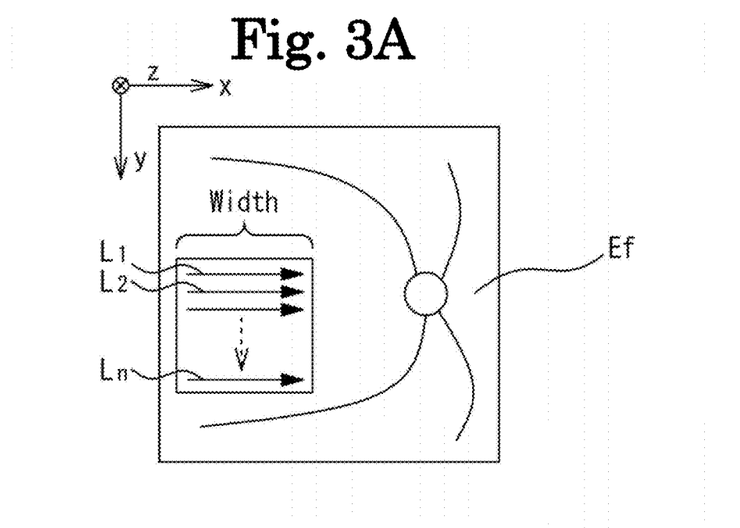
FIGS. 3A to 3C are diagrams for describing obtainment of motion contrast.

FIG. 3A illustrates a scanning line in the fundus. In FIG. 3A, the direction of a z-axis is the optical axis direction of the measurement light. The direction of an x-axis is a left-right direction of a subject, which is perpendicular to the z-axis. The direction of a y-axis is an upper-lower direction of the subject, which is perpendicular to the z-axis. For example, the imaging apparatus 10 obtains a B scan signal by causing the measurement light to be scanned in a direction (for example, an x direction) intersecting with the optical axis direction of the measurement light, along scanning lines $L_1, L_2, \ldots, L_n$ in the fundus Ef. For example, the imaging apparatus 10 performs a plurality of times of B scans of which times are different from each other, in the respective scanning lines, and respectively obtains a plurality of OCT signals of which the times are different from each other.

Figure 3B:
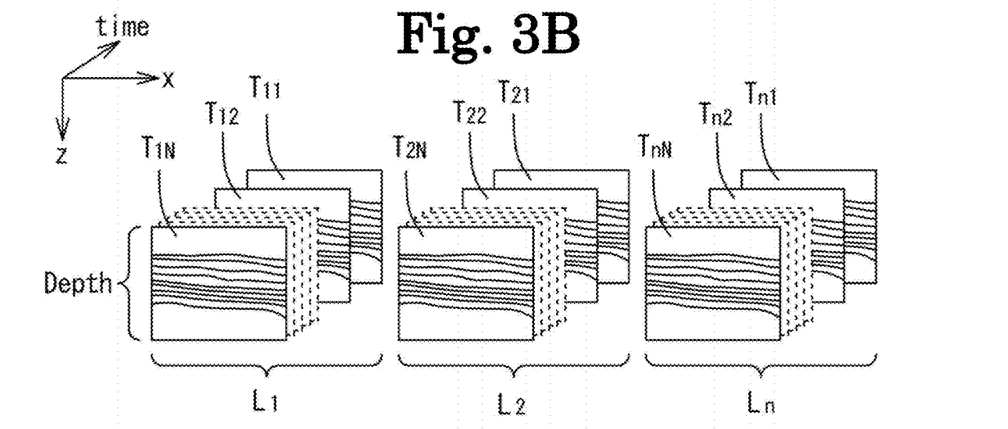

For example, FIG. 3B illustrates the OCT signal that is obtained in a case where the plurality of times of B scans of which the times are different from each other are performed in the scanning lines $L_1, L_2, \ldots, L_n$. For example, FIG. 3B illustrates cases where the scanning line $L_1$ is scanned at times $T_{11}, T_{12}, \ldots, T_{1N}$, the scanning line $L_2$ is scanned at times $T_{21}, T_{22}, \ldots, T_{2N}$, and the scanning line $L_n$ is scanned at times $T_{n1}, T_{n2}, \ldots, T_{nN}$. For example, the imaging apparatus 10 obtains a plurality of OCT data of which the times are different from each other, in the respective scanning lines, and stores the OCT data in the storage portion 11.

Obtainment of Motion Contrast

Figure 3C:
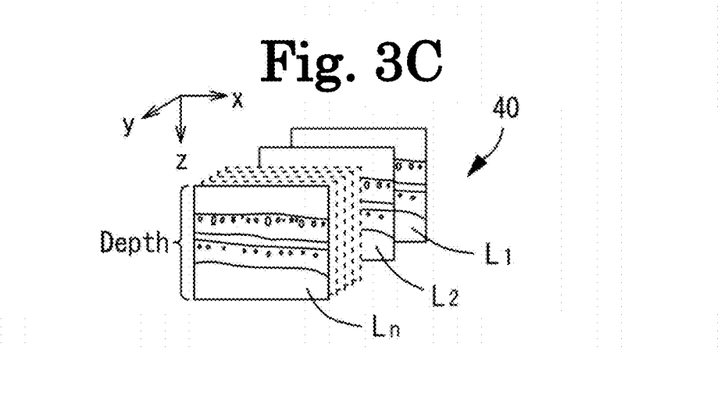

As described above, in a case where the plurality of OCT data which are temporally different from each other with regard to the same position of the subject eye are obtained, it is possible to obtain motion contrast by processing the OCT data. For example, the motion contrast is information grasping a blood flow, a retinal tissue change, and the like of the subject eye. As an arithmetic operation method of the OCT signal for obtaining the motion contrast, for example, a method for calculating an intensity difference of a complex OCT signal, a method for calculating a phase difference of the complex OCT signal, a method for calculating a vector difference of the complex OCT signal, a method for multiplying the phase difference and the vector difference of the complex OCT signal, a method for using the correlation between the signals (correlation mapping), or the like is cited. As one of the arithmetic operation methods, for example, refer to JP-A-2015-131107. FIG. 3C illustrates three-dimensional MC data 40 of the subject eye E which is obtained by aligning motion contrast data (hereinafter abbreviated to MC data) of the scanning lines which are different from each other.

Artifact Reduction Processing

Figure 4A:
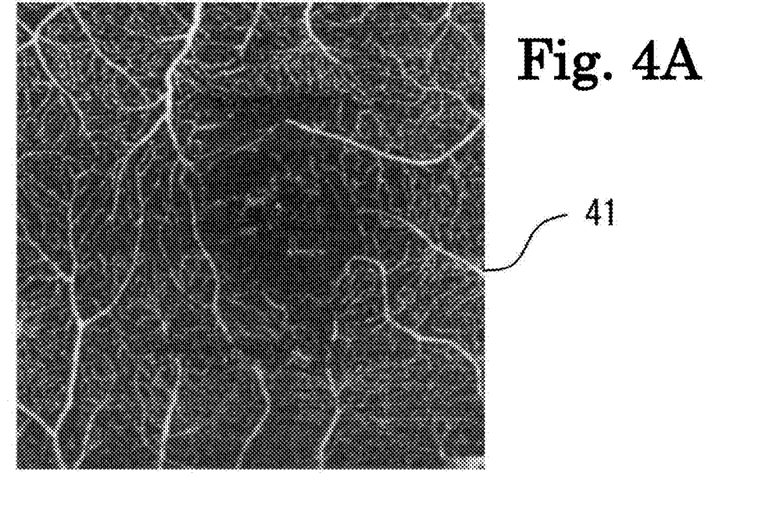
FIGS. 4A and 4B are diagrams illustrating examples of an En face image.
Figure 4B:
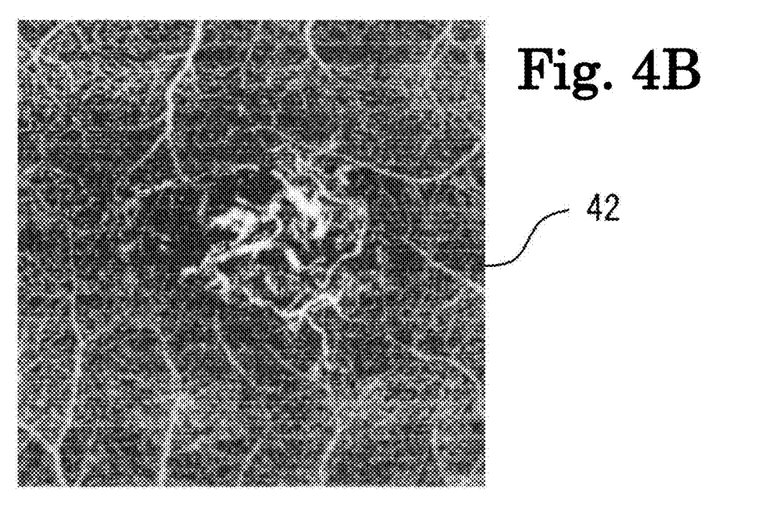

FIG. 4A is an En face image 41 of a retinal shallow layer (surface layer or upper layer) which is constructed based on the MC data 40, and FIG. 4B is an En face image 42 of a retinal deep layer (outer layer or lower layer) which is constructed based on the MC data 40. The En face images are obtained, for example, by pulling out the three-dimensional MC data with regard to a portion of the depth region. For example, the En face image is generated by an integrated value, an average value, or a maximum value in a depth direction on the MC data 40.

In FIGS. 4A and 4B, ideally, since the blood vessels which are depicted in the shallow layer and the deep layer differ from each other, it is considered that the correlation between two images of the En face image 41 and the En face image 42 is small. However, due to the influence of Projection Artifact in which fluctuation (such as a shadow) of the signal deriving from disposition of red blood cells or the like in a blood vessel portion of the retinal shallow layer is imaged on the deep layer in a projection manner, two images become the similar images. Therefore, the image processing portion 72 reduces the influence of Projection Artifact, by making the correlation between two images small.

For example, if the En face image 42 of the deep layer is referred to as "$E_{deep}$", and the En face image 41 of the shallow layer is referred to as "$E_{shallow}$", an En face image "$E_{deep}'$" of the true deep layer from which the artifact is removed is assumed by the following expression (1).

$$E_{deep}' = E_{deep} - wE_{shallow} \quad (1)$$

Here, "w" is the weight of 0 to 1.

The image processing portion 72 calculates the weight "w" that minimizes a correlation "γ" between the image "$E_{shallow}$" of the shallow layer and the image "$E_{deep}'$" of the true deep layer. That is, the weight "w" which satisfies the following expression (2) is calculated.

$$\operatorname{argmin}_w \gamma^2(E_{shallow}, E_{deep}') \quad (2)$$

It is possible to calculate "w" indicated in the expression (2) by the following expression (3) using a covariance "Cov" and a variance "Var".

$$w = Cov(E_{shallow}, E_{deep})/Var(E_{shallow}) \quad (3)$$

Figure 5A:
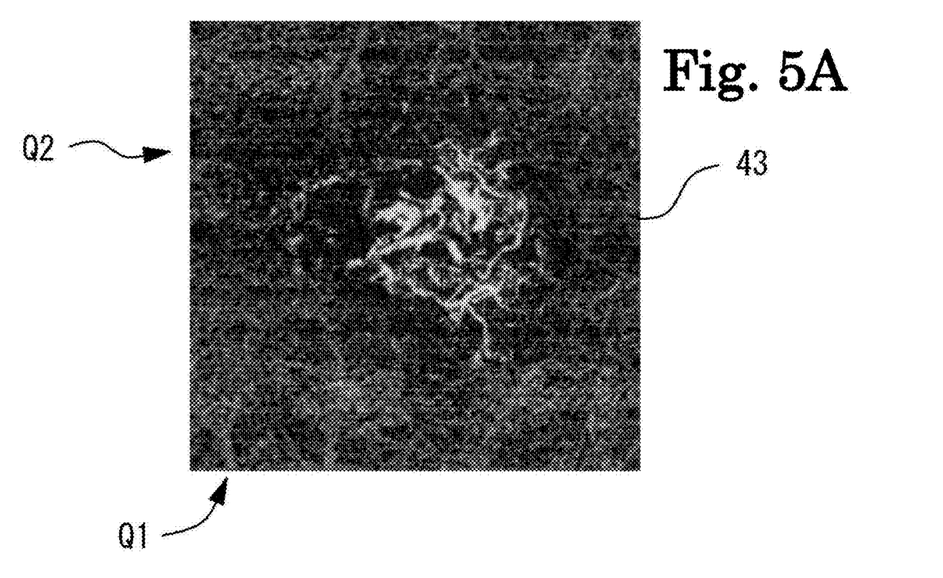
FIGS. 5A and 5B are diagrams illustrating image processing results.

FIG. 5A is a deep layer image 43 obtained by subtracting the image of the shallow layer using the weight which is common with respect to the whole image. As illustrated in FIG. 5A, in a case where the weight which is common with respect to the whole image is used, the artifact may not be locally erased (see an arrow Q1), or may be erased too much (see an arrow Q2), and there is a case where the image from which the influence of the blood vessel of the shallow layer is not capable of being removed is obtained.

Figure 6:
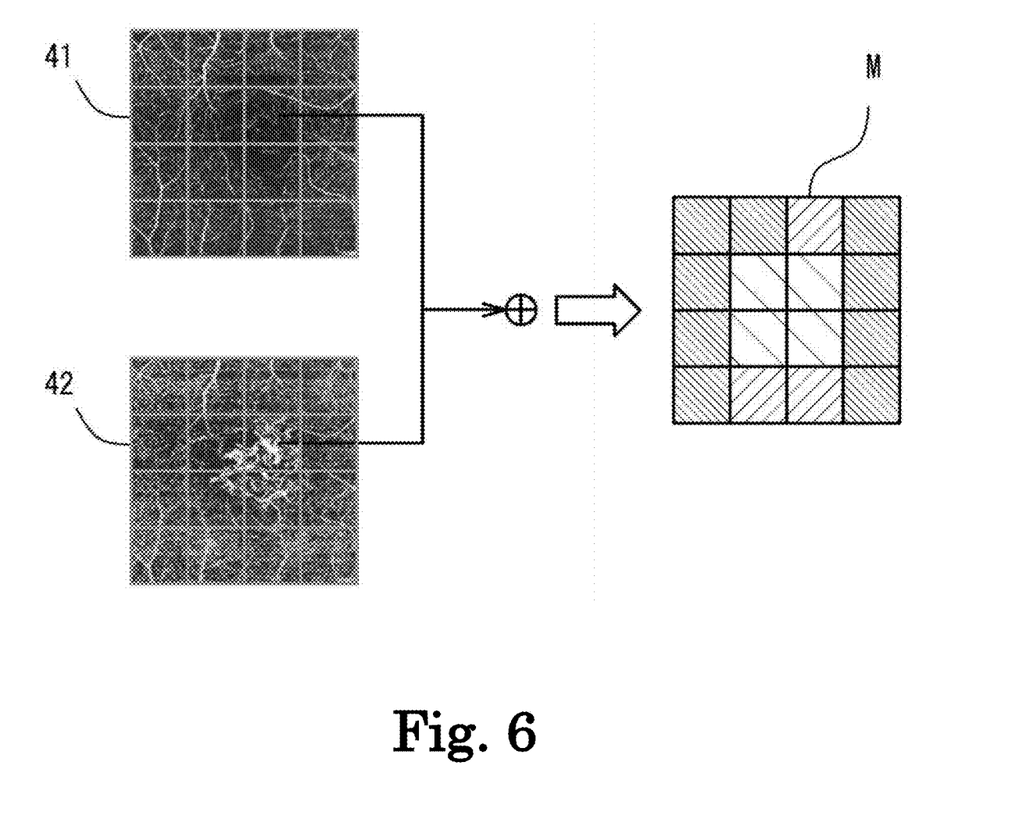
FIG. 6 is a diagram for describing an image processing method.

Therefore, in the present embodiment, the correlation between the image "$E_{shallow}$" of the shallow layer and the image "$E_{deep}'$" of the deep layer is minimized per the local area. Specifically, as illustrated in FIG. 6, the image is divided into several blocks. Therefore, the correlation is calculated per block, and the weight is determined. In the example illustrated in FIG. 6, the image is divided into 16 blocks of 4×4, and a weight map M is calculated based on the correlations between the respective blocks.

Figure 5B:
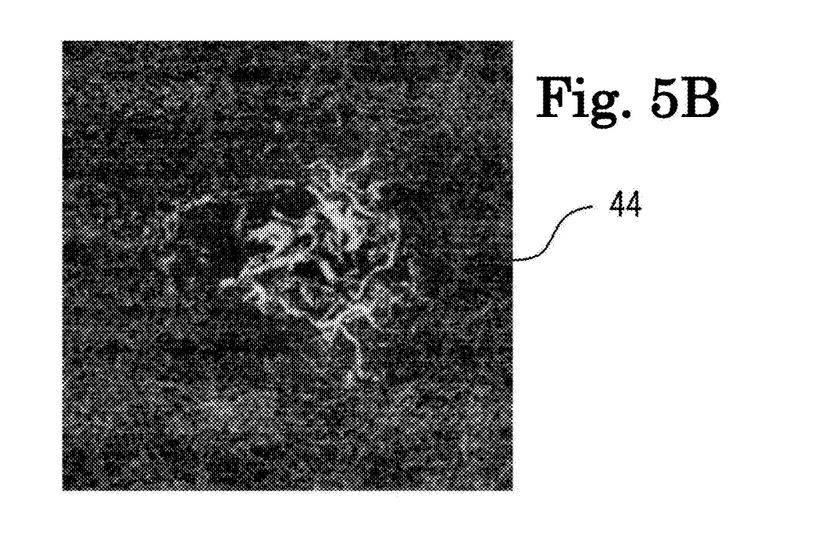

In the case of FIG. 6, since the weight is calculated per the local area, the weight becomes large because the correlation becomes high in the block with a lot of artifacts. On the other hand, since the correlation becomes low in the block with few artifacts, the weight is calculated to be small. In this manner, the weight which is calculated per block is used, thereby, it is possible to prevent the artifact from remaining in a deep layer image 44 after subtraction processing, or the artifact from being erased too much (see FIG. 5B).

In the above examples, the image is divided into 16 blocks of 4×4, but the present disclosure is not limited thereto. The number of divisions, and a size of the block may be any. For example, the image processing portion 72 may set the number of divisions, the size, the position, or the like of the block in accordance with angle of view of the image, a scan position, scan density, the similarity degree between the shallow layer image and the deep layer image, the depth of the layer, or the like. For example, the image processing portion 72 may set the division position of the image, based on the information of the shallow layer. Specifically, the image processing portion 72 may set the position at which the image is divided, based on the position of the blood vessel that is detected from the shallow layer image. In this manner, the division position of the image is automatically set, thereby, an area with a lot of vessels in which the artifact is generated, and an area with a few vessels in which the artifact is generated are efficiently separated from each other, and it is possible to calculate the more suitable weight. Naturally, the shape of dividing the image may be acceptable even if it is not the block shape, and the shape may be the shape of concentric circles, or may be any shape. In a case where the difference in weight between the adjacent blocks is large, there is a possibility that an edge is generated in the image after the subtraction processing. In order to prevent the possibility, the change of the weight on the weight map may be smoothened.

In the above examples, the correlation is calculated by a unit of block, but the correlation may be calculated by a unit of pixel. In this case, for example, the correlation may be calculated regarding the pixel of a predetermined range with each pixel as a center, and the weight of a center pixel may be determined.

The image processing portion 72 may perform the calculation such that the correlation is calculated only in an area in which the blood vessel exists in the shallow layer, and the correlation is not calculated in an area in which the blood vessel does not exist in the shallow layer, among the divided areas.

Regarding Range of Shallow Layer (Shallow Slab)

Figure 7A:
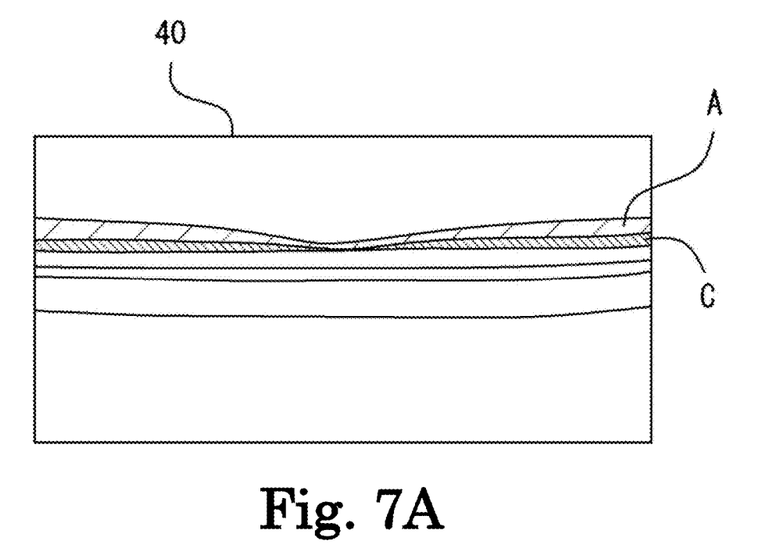
FIGS. 7A and 7B are diagrams illustrating arithmetic operation ranges of image processing.
Figure 7B:
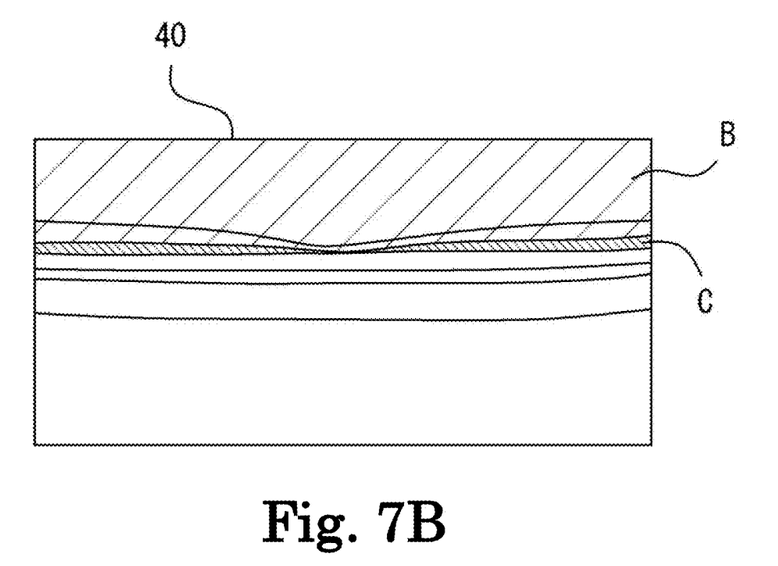

At the time of calculating the correlation between the shallow layer and the deep layer, the image processing portion 72 may perform the calculation to be capable of changing a range in which the image of the shallow layer is constructed. FIGS. 7A and 7B are diagrams illustrating construction ranges of the En face image in the three-dimensional MC data 40. For example, as illustrated in FIG. 7A, in a case where a predetermined range A (for example, a range of IPL/INL+90 μm from ILM) is used as the range (depth region) of the shallow layer, the influence is exerted by a segmentation error of the ILM, or the blood vessel (such as a neovessel) in an upper portion of the ILM or a foreign substance (such as proliferative membrane) in the vitreous body does not become a target of the arithmetic operation. Accordingly, there is a possibility that Projection Artifact is not capable of being appropriately removed. The ILM (Internal Limiting Membrane) is an inner limiting membrane, the IPL (Inner Plexiform Layer) is an inner reticular layer, and the INL (Inner Nuclear Layer) is an inner granular layer.

In the present embodiment, as illustrated in FIG. 7B, a range B which is to an upper portion of the MC data 40 from an upper end of a construction range C of the En face image of the deep layer of an artifact removal target is referred to as a shallow layer, and the arithmetic operation of the artifact removal is performed. That is, the data region of an upper side than the construction range C in the MC data 40 is referred to as a shallow layer. Thereby, it is possible to perform the arithmetic operation of the artifact removal in any range without being influenced by the result of the segmentation.

There is a case where the shallow layer includes Fixed pattern noise in an upper portion of the OCT image, or the noise due to a coherence revival phenomenon (in the case of SS-OCT). Accordingly, the image processing portion 72 may carry out processing of reducing the noise in the upper portion of the OCT image. For example, the image processing portion 72 may store the position of the noise in advance, and may perform the processing such that the noise position is not included in the range of the shallow layer.

Control Operation

Figure 8:
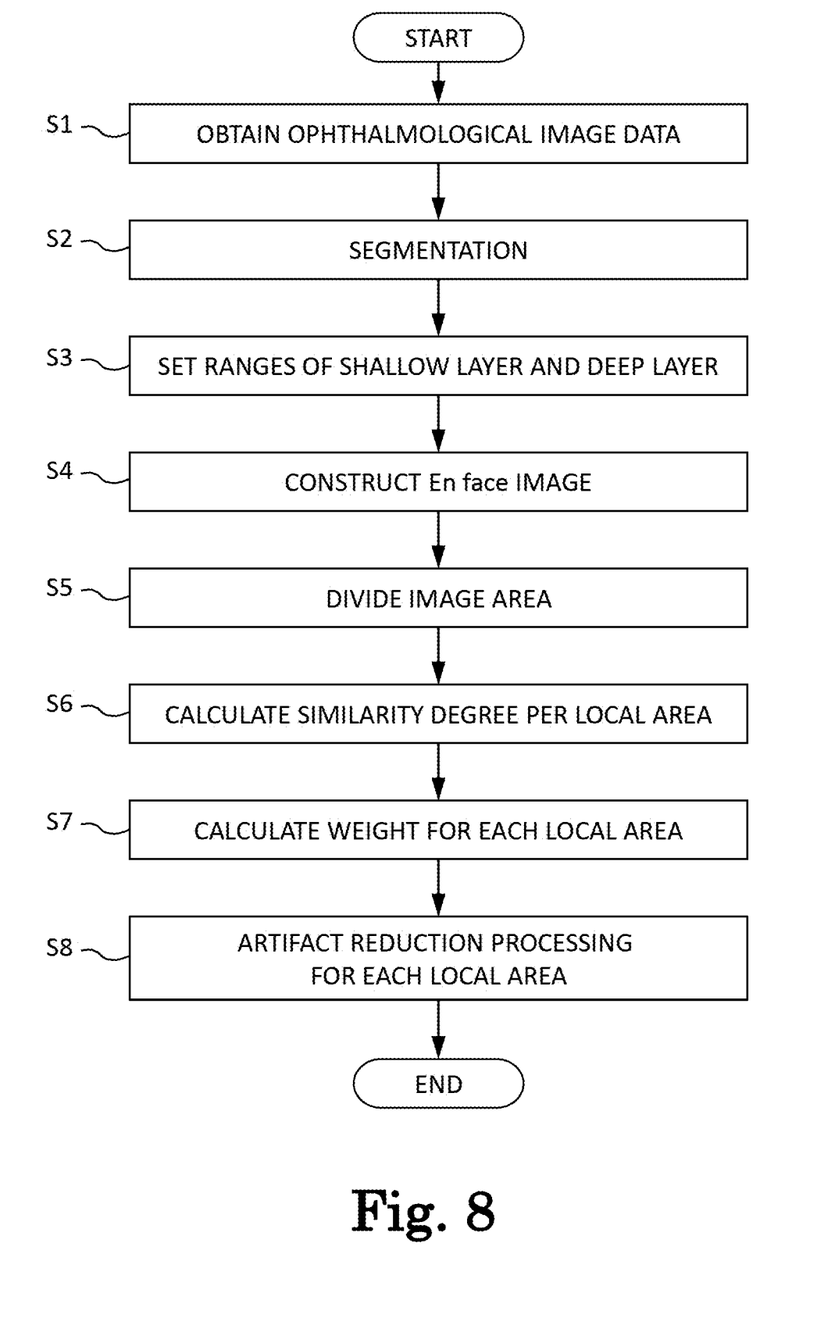
FIG. 8 is a flowchart of a control operation.

An example of a control operation of the ophthalmological image processing apparatus 1 will be described based on FIG. 8. First, the image obtaining portion 71 obtains the ophthalmological image data (for example, the OCT data) from the storage portion 11 of the imaging apparatus 10 through the communication unit (step S1). Thereafter, the image processing portion 72 performs the segmentation of the ophthalmological image data (step S2). For example, the image processing portion 72 detects a boundary of the retinal layer by the processing such as edge detection, and performs the segmentation of the ophthalmological image. The image processing portion 72 sets the construction range of the En face image of the shallow layer and the construction range of the En face image of the deep layer (step S3), and constructs each image (step S4). If the respective En face images of the shallow layer and the deep layer are constructed, the image processing portion 72 divides the image into the plurality of areas (step S5), and calculates the similarity degree per the local area (step S6). Next, the image processing portion 72 determines the weight based on the similarity degree per the local area (step S7), and performs the artifact reduction processing (for example, the subtraction processing) of the En face image of the deep layer based on the weight (step S8).

In the above examples, a case where the image processing portion 72 performs the artifact reduction processing of the En face image based on the motion contrast data is described, but the image processing portion 72 may perform the same processing on the En face image based on the normal OCT signal.

In the above examples, the imaging apparatus 10 includes the OCT optical system, but the present disclosure is not limited thereto. For example, the imaging apparatus 10 may include an SLO optical system, or may include a configuration of a fundus camera. In the fundus imaging apparatuses, in a case where a fluorescent contrast image is imaged, the noise reduction processing described above may be performed, regarding an image of the retinal shallow layer which is imaged by FA imaging (fluorescein fluorescent contrast imaging), and an image of the choroid coat which is imaged by IA imaging (indocyanine green fluorescent contrast imaging). In this case, since the blood vessel in the surface portion of the retina which is projected in the image of the IA imaging is removed, it is possible to obtain an image on which the blood vessel of the choroid coat is easily observed.

A characteristic in which invasion depth degrees of the light differ from each other in accordance with wavelengths may be used. Since the fundus camera and the SLO is capable of obtaining the En face images of which the depths are different from each other per channels such as red, green, and blue (refer to JP-A-2018-000619), the image processing portion 72 may calculate the correlation between the images of the respective channels per the local area, and may determine the weight, thereby, the image processing portion 72 may remove the artifact of the deep layer image.

1 ophthalmological image processing apparatus
10 imaging apparatus
70 controller
100 OCT optical system

What is claimed is:

1. An ophthalmological image processing apparatus that processes an ophthalmological image, comprising:
   an image obtaining portion configured to obtain ophthalmological image data, which is captured by an imaging unit, of a subject eye; and
   an image processing portion configured to process the ophthalmological image data,
   wherein the image processing portion uses a first front image of the subject eye captured in a first depth region to correct a second front image of the subject eye captured in a second depth region which is different from the first depth region, and
   the first front image and the second front image are constructed based on the ophthalmological image data.

2. The ophthalmological image processing apparatus of claim 1,
   wherein the image processing portion uses the first front image to correct the second front image per a local area which is a section obtained by dividing the first front image and the second front image.

3. The ophthalmological image processing apparatus of claim 2,
   wherein the image processing portion corrects the second front image such that a similarity degree between the first front image and the second front image reduces in each of the local area.

4. The ophthalmological image processing apparatus of claim 3,
   wherein the image processing portion sets a weight for each local area based on the similarity degree which is calculated per the local area, and corrects the second front image in accordance with the weight.

5. The ophthalmological image processing apparatus of claim 1,
   wherein the first front image is constructed based on the ophthalmological image data in a first data region which is shallower than a second data region in which the second front image is constructed.

6. The ophthalmological image processing apparatus of claim 5, wherein the image processing portion excludes a fixed noise area from the first data region.

7. A non-transitory computer readable recording medium storing an ophthalmological image processing program used in an ophthalmological image processing apparatus that processes an ophthalmological image,
wherein the ophthalmological image processing program is executed by a controller of the ophthalmological image processing apparatus to cause the ophthalmological image processing apparatus to perform:
obtaining ophthalmological image data, which is captured by an imaging unit, of a subject eye; and
using a first front image of the subject eye captured in a first depth region to correct a second front image of the subject eye captured in a second depth region which is different from the first depth region, and
the first front image and the second front image are constructed based on the ophthalmological image data.

* * * * *